US008913816B2

(12) United States Patent
Chono

(10) Patent No.: US 8,913,816 B2
(45) Date of Patent: Dec. 16, 2014

(54) MEDICAL IMAGE DIANOSTIC DEVICE, REGION-OF-INTEREST SETTING METHOD, AND MEDICAL IMAGE PROCESSING DEVICE

(75) Inventor: Tomoaki Chono, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 453 days.

(21) Appl. No.: 13/259,358

(22) PCT Filed: Apr. 5, 2010

(86) PCT No.: PCT/JP2010/056151
§ 371 (c)(1),
(2), (4) Date: Sep. 23, 2011

(87) PCT Pub. No.: WO2010/116965
PCT Pub. Date: Oct. 14, 2010

(65) Prior Publication Data
US 2012/0014588 A1 Jan. 19, 2012

(30) Foreign Application Priority Data
Apr. 6, 2009 (JP) ................................. 2009-092216

(51) Int. Cl.
*G06K 9/00* (2006.01)
*A61B 8/00* (2006.01)
*A61B 8/08* (2006.01)
*G06T 7/20* (2006.01)

(52) U.S. Cl.
CPC . *A61B 8/00* (2013.01); *A61B 8/469* (2013.01); *A61B 8/0883* (2013.01);
(Continued)

(58) Field of Classification Search
CPC ........... G06K 9/00; G06K 9/46; A61B 6/032; A61B 8/00; A61B 8/0883; A61B 8/469; A61B 5/00; A61B 8/483; A61B 8/5276
USPC ......... 382/128, 131, 154, 162, 165, 173, 175, 382/190, 195, 199, 254, 256, 260; 128/922; 356/39; 377/10
See application file for complete search history.

(56) References Cited

U.S. PATENT DOCUMENTS

2002/0087061 A1* 7/2002 Lifshitz et al. ................. 600/407
2003/0174890 A1* 9/2003 Yamauchi ...................... 382/199
(Continued)

FOREIGN PATENT DOCUMENTS

JP 8-131436 5/1996
JP 10-323349 12/1998
(Continued)

OTHER PUBLICATIONS

Myocardial Motion Analysis From B-Mode Echocardiograms by Arigovidan M et al., vol. 14, No. 4, Apr. 1, 2005, pp. 525-536.
(Continued)

*Primary Examiner* — Chan Park
*Assistant Examiner* — Mia M Thomas
(74) *Attorney, Agent, or Firm* — Brundidge & Stanger, P.C.

(57) ABSTRACT

The medical image diagnosis device of the invention includes image generating means configured to obtain image data of a tissue of an object and generate an image of the tissue of the object based on the image data, calculation means configured to calculate at least one of brightness and motion vectors of plural measurement points of the generated image, input means configured to specify an observation region of the image, a database in which a characteristic amount of at least one of the brightness and the motion vectors of the measurement points in respective images of plural different observation regions is set and stored in advance, checking means configured to read the characteristic amount of the observation region that is specified through the input means from the database and check the characteristic amount with results of calculation performed on the generated image by the calculation means, and ROI setting means configured to set a region of interest in the generated image based on checked results of the checking means.

12 Claims, 16 Drawing Sheets

(52) U.S. Cl.
CPC ............... *A61B 8/5276* (2013.01); *A61B 8/585* (2013.01); *G06T 7/2006* (2013.01); *A61B 8/483* (2013.01); *G06T 2207/10132* (2013.01); *G06T 2207/30048* (2013.01)
USPC ............................. 382/131; 382/154; 382/203

(56) References Cited

U.S. PATENT DOCUMENTS

| | | | |
|---|---|---|---|
| 2004/0228508 A1* | 11/2004 | Shigeta | 382/124 |
| 2006/0029269 A1* | 2/2006 | Matsuoka | 382/132 |
| 2006/0034513 A1* | 2/2006 | Cai et al. | 382/173 |
| 2006/0039583 A1* | 2/2006 | Bickert et al. | 382/103 |
| 2006/0251303 A1* | 11/2006 | He et al. | 382/128 |
| 2007/0015994 A1* | 1/2007 | Hong et al. | 600/407 |
| 2007/0239014 A1* | 10/2007 | Yoshikawa et al. | 600/454 |
| 2008/0095417 A1* | 4/2008 | Pedrizzetti et al. | 382/128 |
| 2008/0181479 A1* | 7/2008 | Yang et al. | 382/131 |
| 2008/0262354 A1* | 10/2008 | Yoshida et al. | 600/443 |
| 2009/0112088 A1* | 4/2009 | Ohuchi et al. | 600/438 |
| 2009/0141935 A1* | 6/2009 | Grass et al. | 382/103 |
| 2009/0185728 A1* | 7/2009 | Klingenbeck-Regn | 382/128 |
| 2010/0179414 A1* | 7/2010 | Kuhn et al. | 600/411 |
| 2010/0185085 A1* | 7/2010 | Hamilton | 600/437 |
| 2010/0208962 A1* | 8/2010 | Roessl et al. | 382/131 |
| 2011/0063950 A1* | 3/2011 | Greenleaf et al. | 367/87 |
| 2011/0251505 A1* | 10/2011 | Narayan et al. | 600/515 |

FOREIGN PATENT DOCUMENTS

| | | |
|---|---|---|
| JP | 2001 161695 | 6/2001 |
| JP | 2003-250804 | 9/2003 |
| JP | 2005 40301 | 2/2005 |
| JP | 2006-231035 | 9/2006 |
| JP | 2007-125273 | 5/2007 |
| JP | 2007-190172 | 8/2007 |
| JP | 2007 330764 | 12/2007 |
| JP | 2008 161220 | 7/2008 |
| WO | 2005059586 | 6/2005 |
| WO | 2008/044441 | 4/2008 |

OTHER PUBLICATIONS

International Search Report for PCT International Application No. PCTJP2010/056151 mailed Apr. 27, 2010.

* cited by examiner

MEDICAL IMAGE DIANOSTIC DEVICE, REGION-OF-INTEREST SETTING METHOD, AND MEDICAL IMAGE PROCESSING DEVICE

TECHNICAL FIELD

The present invention relates to a medical image diagnosis device, a region-of-interest setting method, and a medical image processing device. Particularly, the invention relates to a technique of automatically setting a region of interest (ROI) in a tomographic image of a cross-sectional region of an object.

BACKGROUND ART

A medical image diagnosis device such as an ultrasonic diagnosis device, an X-ray CT device, a magnetic resonance imaging (MRI) device, and the like, which obtains image data of a tissue in a cross-sectional region of an object and displays a tomographic image by generating the tomographic image based on the image data, is known. For example, the ultrasonic diagnosis device transmits ultrasonic waves into the inside of the object from an ultrasonic probe, and receives reflected echo signals of the ultrasonic waves according to the structure of the body tissue from the inside of the object, thereby generating and displaying a tomographic image such as a B-mode image, for example.

It is known that in the medical image diagnosis device, the ROI is set so as to observe and measure in detail a specific region included in the tomographic image. That is, by setting the ROI in a region drawing attention, it is possible to display or measure in detail information in the ROI, instead of making information outside the ROI become sparse. For example, when the size of ROI is narrowed down in color Doppler imaging of ultrasonic diagnosis, only a narrow scanning range in the ROI is subjected to Doppler analysis. Accordingly, an effect of improving temporal resolution is obtained.

In order to set the ROI, it is necessary to adjust the position and size of the ROI for each observation region. However, since an examiner has hitherto had to manually set the ROI using an input instrument such as a trackball, there is a burden on the examiner.

In this respect, as disclosed in PTL 1 for example, a system has been proposed which reduces the burden on the examiner by setting a Doppler sample point based on a position of a maximum blood flow rate in an image of color flow mapping.

CITATION LIST

Patent Literature

[PTL 1] Japanese Patent No. 3403917

SUMMARY OF INVENTION

Problems to be Solved by the Invention

However, the technique disclosed in PTL 1 does not consider setting the region of interest in various observation regions of an object other than a blood flow position, which do not have an index such as the maximum blood flow rate, using a computer.

Therefore, the technique does not consider setting the ROI in an observation region in which the Doppler measurement cannot be easily performed or setting the ROI in observation regions other than the blood flow position.

Accordingly, an object of the invention is to provide novel indices for setting the region of interest in various observation regions of the object.

Solution to Problem

The medical image diagnosis device of the invention includes image generating means for obtaining image data of a tissue of an object and generating an image of the tissue of the object based on the image data, calculation means for calculating at least one of brightness and motion vectors of plural measurement points of the generated image, input means for specifying an observation region of the image, a database in which a characteristic amount of at least one of the brightness and the motion vectors of the measurement points in respective images of plural different observation regions is set and stored in advance, checking means for reading the characteristic amounts of the observation region that is specified through the input means from the database and checking the characteristic amount with results of calculation performed on the generated image by the calculation means, and ROI setting means for setting a region of interest in the generated image based on the checked results of the checking means.

In addition, the medical image diagnosis device of the invention includes tomographic image generating means for obtaining image data of a tissue of a cross-sectional region of an object and generating a tomographic image based on the image data, calculation means for calculating at least one of brightness and motion vectors of plural measurement points of the generated tomographic image, input means for specifying an observation region of the tomographic image, a database in which a characteristic amount of at least one of the brightness and the motion vectors of the measurement points in respective tomographic images of plural different observation regions is set and stored in advance, checking means for reading the characteristic amount of the observation region that is specified through the input means from the database and checking the characteristic amount with results of calculation performed on the generated tomographic image by the calculation means, and ROI setting means for setting a region of interest in the generated tomographic image based on the checked results of the checking means.

That is, when the user specifies a region (observation region) for which it is desired to set a region of interest through the input means, the characteristic amount of the specified observation region is read from the database and checked with the image, and the region of interest is set in the image based on the checked results. Accordingly, if the characteristic amount of various observation regions of the object, that is, unique characteristics of the observation regions which appear in at least one of the brightness and motion vectors of the measurement points of images of respective observation regions are determined as novel indices for setting the region of interest and then stored in the database in advance, it is possible to automatically set the region of interest in various observation regions of the object.

In this case, it is possible to set the characteristic amount based on at least one of a distribution pattern of the brightness, a distribution pattern of the motion vectors, and the magnitude and direction of the motion vectors of measurement points of the respective images of plural different observation regions. That is, in the distribution pattern of the brightness and the distribution pattern of the motion vectors of the measurement points of the images, the unique characteristics of the respective observation regions appear. Therefore, the unique characteristics can be used as the characteristic amount. In addition, for example, when the heart of the object is observed, since the cardiac valve moves faster than other regions, the characteristic amount of the cardiac valve can also be set in a logical form such as "a position where motion vectors are maximal".

The characteristic amount can also include the one which is set based on contour information of a cardiac chamber region that is surrounded by an intra-cardiac chamber wall surface and a valve annulus surface, which is extracted from the distribution pattern of the brightness of the plural measurement points in the cardiac image of the object. For example, both the end points of the contour of the intra-cardiac chamber wall corresponding to the intra-cardiac chamber wall surface become valve annulus portions corresponding to a starting point of the valve annulus surface, and the vertex of the contour of the intra-cardiac chamber wall becomes the cardiac apex. Consequently, these facts can be set in advance as the characteristic amount. When the cardiac blood flow is desired to be observed, midpoints of two valve annulus portions can be set in advance as the characteristic amount, for example.

It is also possible to display the region of interest that is set automatically by the ROI setting means together with the generated image on display means, and to cause the region of interest to follow the motion vectors of the plural measurement points of the image. In this manner, once the region of interest is set in the observation region, the region of interest follows the movement of a tissue. As a result, the examiner does not need to reset the regions of interest one by one, whereby the burden on the examiner can be reduced.

A region-of-interest setting method of the invention includes a step of obtaining image data of a tissue of an object and generating an image of the tissue of the object based on the image data, a step of calculating at least one of brightness and motion vectors of plural measurement points of the generated image, a step of specifying an observation region of the image, a step of reading a characteristic amount of the observation region that is specified in the step of specifying an observation region from a database in which the characteristic amount of at least one of the brightness and the motion vectors of the measurement points in respective images of plural different observation regions is set and stored, and checking the characteristic amount with at least one of the brightness and the motion vectors of the plural measurement points of the generated image, and a step of setting a region of interest in the generated image based on the checked results.

A medical image processing device of the invention includes image input means for inputting an image of a tissue of an object, which is generated in advance, calculation means for calculating at least one of brightness and motion vectors of plural measurement points of the input image, input means for specifying an observation region of the image, checking means for reading a characteristic amount of the observation region that is specified by the input means from a database in which the characteristic amount of at least one of the brightness and the motion vectors of the measurement points in respective images of plural different observation regions is set and stored, and checking the characteristic amount with results of the calculation performed on the image by the calculation means, and ROI setting means for setting a region of interest in the image based on the checked results of the checking means.

A region-of-interest setting program of the invention includes a step of calculating at least one of brightness and motion vectors of plural measurement points of an image of a tissue of an object, which is generated in advance, a step of specifying an observation region of the image, a step of reading a characteristic amount of the observation region that is specified in the step of specifying an observation region from a database in which the characteristic amount of at least one of the brightness and the motion vectors of the measurement points in respective images of plural different observation regions is set and stored, and checking the characteristic amount with at least one of the brightness and the motion vectors of the plural measurement points of the image, and a step of setting a region of interest in the image based on the checked results.

Advantageous Effects of Invention

According to the invention, it is possible to provide novel indices for setting a region of interest in various observation regions of an object.

DESCRIPTION OF EMBODIMENTS

Hereinafter, examples of a medical image diagnosis device, a region-of-interest setting method, a medical image processing device, and a region-of-interest setting program to which the invention is applied will be described. The examples describe an ultrasonic diagnosis device as an example of the medical image diagnosis device. However, the invention can be applied to a device which generates and displays a tomographic image of a tissue in a cross-sectional region of an object, such as an X-ray CT device, a magnetic resonance imaging (MRI) device, and the like, in addition to the ultrasonic diagnosis device.

EXAMPLE 1

Figure 1:
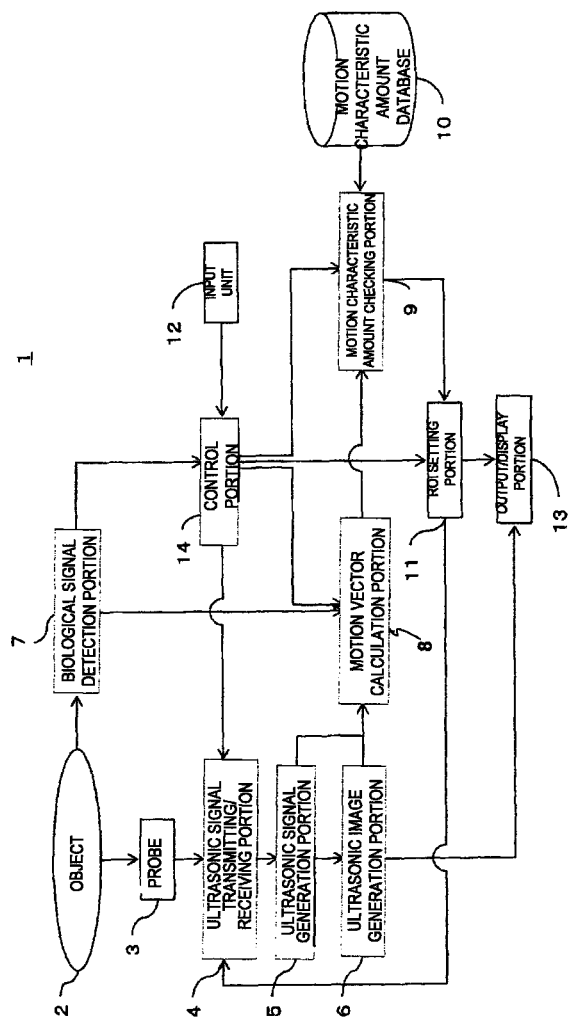
FIG. 1 is a block diagram showing a schematic configuration of Example 1 of an ultrasonic diagnosis device.

FIG. 1 is a block diagram showing a schematic configuration of Example 1 of the ultrasonic diagnosis device to which the invention is applied. An ultrasonic diagnosis device 1 shown in FIG. 1 is based on a well-known ultrasonic diagnosis device and makes an ultrasonic diagnosis by using two or three dimensional signals. The ultrasonic diagnosis device 1 includes a probe 3, an ultrasonic signal transmitting and receiving portion 4, an ultrasonic signal generation portion 5, an ultrasonic image generation portion 6, a biosignal detection portion 7, a motion vector calculation portion 8, a motion characteristic amount checking portion 9, a motion characteristic amount database 10, a ROI setting portion 11, an input portion 12, an output and display portion 13, and a control portion 14.

The probe 3 is a device which transmits and receives ultrasonic waves to and from an object 2 and converts the ultrasonic waves into electric signals. The probe 3 uses a linear type, a convex type, a sector type, and other types of beam scanning method.

The ultrasonic signal transmitting and receiving portion 4 transmits and receives the ultrasonic signals converted into the electric signal to and from the probe. The ultrasonic signal transmitting and receiving portion 4 receives information on the power and timings of the transmitting and receiving from the control portion 14, or a beam scanning range from the ROI setting portion 11, whereby the transmitting and receiving is controlled so that a desired ultrasonic signal is obtained.

The ultrasonic signal generation portion 5 performs a signal processing on the signal received from the ultrasonic signal transmitting and receiving portion 4, according to setting for imaging of the device through a phasing circuit and an amplifier circuit, thereby obtaining shaped ultrasonic signals.

The ultrasonic image generation portion 6 performs a signal processing on the signal received from the ultrasonic signal generation portion 5, according to setting for imaging of the ultrasonic diagnosis device through an amplifier circuit and a detector circuit, thereby generating an ultrasonic image. Tomographic image generating means is configured with the probe 3, the ultrasonic signal transmitting and receiving portion 4, the ultrasonic signal generation portion 5, and the ultrasonic image generation portion 6.

The biosignal detection portion 7 detects biosignals of the object 2 and converts the biosignals into a signal data. Examples of the biosignal include ECG (electrocardiogram) and PCG (phonocardiogram).

At timings and positions specified by the control portion 14, the motion vector calculation portion 8 performs a statistical processing such as averaging, dispersion, and the like on the motion vectors of plural measurement points of the tomographic image of the object 2 and other motion vectors by using the ultrasonic signals output from the ultrasonic signal generation portion 5 or the amplitude pattern of the ultrasonic image output from the ultrasonic image generation portion 6, thereby calculating the characteristic amount from which noise has been removed.

The motion characteristic amount checking portion 9 checks the motion vectors output from the motion vector calculation portion 8 or the characteristic amount of motion vectors with the characteristic amount which is stored in the motion characteristic amount database 10 in association with the observation region specified through the input portion 12, thereby detecting the desired position of the ROI. The motion characteristic amount checking portion 9 also determines the shape of the ROI according to measurement items specified by the input portion 12.

In the motion characteristic amount database 10, the characteristic amount of the motion vectors of measurement points in the respective tomographic images of plural different observation regions where the ROI is set is set and stored in advance. For example, the distribution pattern of the motion vectors of plural measurement points in the tomographic images of the respective observation regions, the data on the magnitude and direction of the motion vectors of the ROI in a certain time phase, and a logic such as "position where magnitude of motion vector yields extreme value" are recorded in the database. In addition, the information on the shape of the ROI which should be set for each of the observation regions and the measurement items is stored in the database.

The ROI setting portion 11 sets the ROI based on the results of checking performed by the motion characteristic amount checking portion 9. The ROI has a two or three dimensional shape according to the measurement item. The ROI also includes a ROI with a defined width such as Doppler sample gate.

The input portion 12 is an input instrument that the examiner uses to specify a region for which it is desired to set the measurement items and the ROI as an observation region. The input portion 12 includes a keyboard, a trackball, switches, and the like.

The output and display portion 13 displays the ultrasonic image output from the ultrasonic image generation portion 6 and the ROI set by the ROI setting portion 11 by superimposing the ultrasonic image and ROI on each other, and outputs a measurement position data based on the ROI set by the ROI setting portion 11 to a measurement and calculation portion. The measurement and calculation portion performs various types of calculations and analyses in the ROI set by the ROI setting portion 11.

The control portion 14 controls processing timings of each portion based on the instruction from the input portion 12 and the signal from the biosignal detection portion 7.

Figure 2:
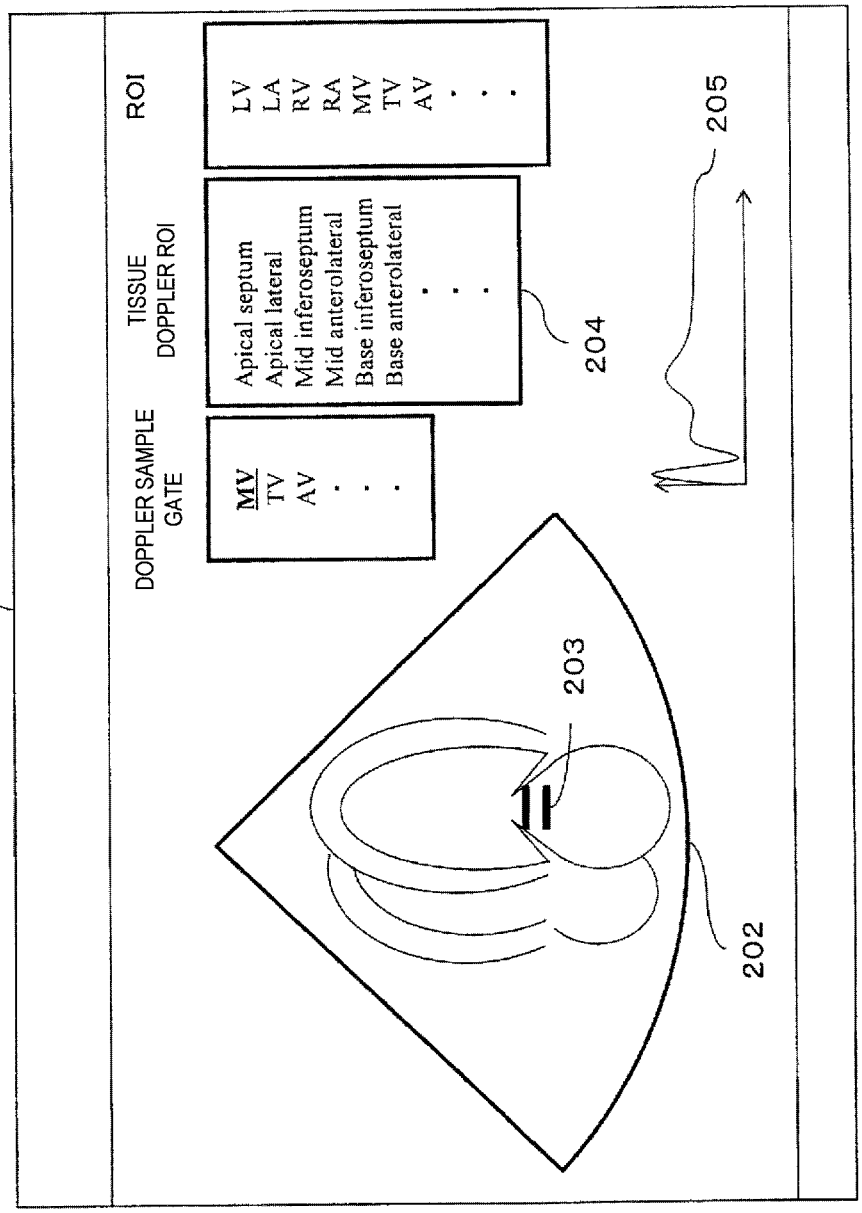
FIG. 2 is a view showing a measurement screen of Example 1 of the ultrasonic diagnosis device.

The flow in operating the ultrasonic diagnosis device of the example will be described using FIG. 2. The examiner draws a tomographic image by touching the probe 3 to an object as in a normal examination. FIG. 2 is a view showing a measurement screen 201 of the ultrasonic diagnosis device of the present embodiment, which is displayed when an apical 4-chamber view 202 of the heart is observed. Herein, the examiner sets the ROI so as to observe the tissue closely by zooming in or to set a window of a Doppler measurement. The types of the ROI setting position are made into a list and displayed as a list 204 on the screen. Accordingly, the observation region for which it is desired to set the ROI is selected from the list 204 through the input portion 12. The ultrasonic diagnosis device 1 sets the position of the ROI based on the selected type of the ROI.

FIG. 2 shows an example of selecting the Doppler sample gate of MV (Mitral Valve) from the list 204. Herein, as the ROI selected in the apical 4-chamber view 202 of the heart, a Doppler sample gate 203 of MV is displayed. When the position of the ROI deviates from a desired position, the position is finely adjusted manually through the input portion 12. Thereafter, even if the position of the tissue further moves in the image due to a following function, the ROI moving along this movement is displayed as a moving image for each frame. In addition, as shown in FIG. 2, a biosignal 205 of the object 2 that is detected by the biosignal detection portion 7 may be displayed in a time-series manner.

Selecting the observation region for which it is desired to set the ROI from the list is the only operation performed by the examiner. Accordingly, it is possible to reduce the burden on the examiner of setting the size of the ROI while moving the position of the ROI by using an input instrument such as a trackball as in the past.

Figure 3:
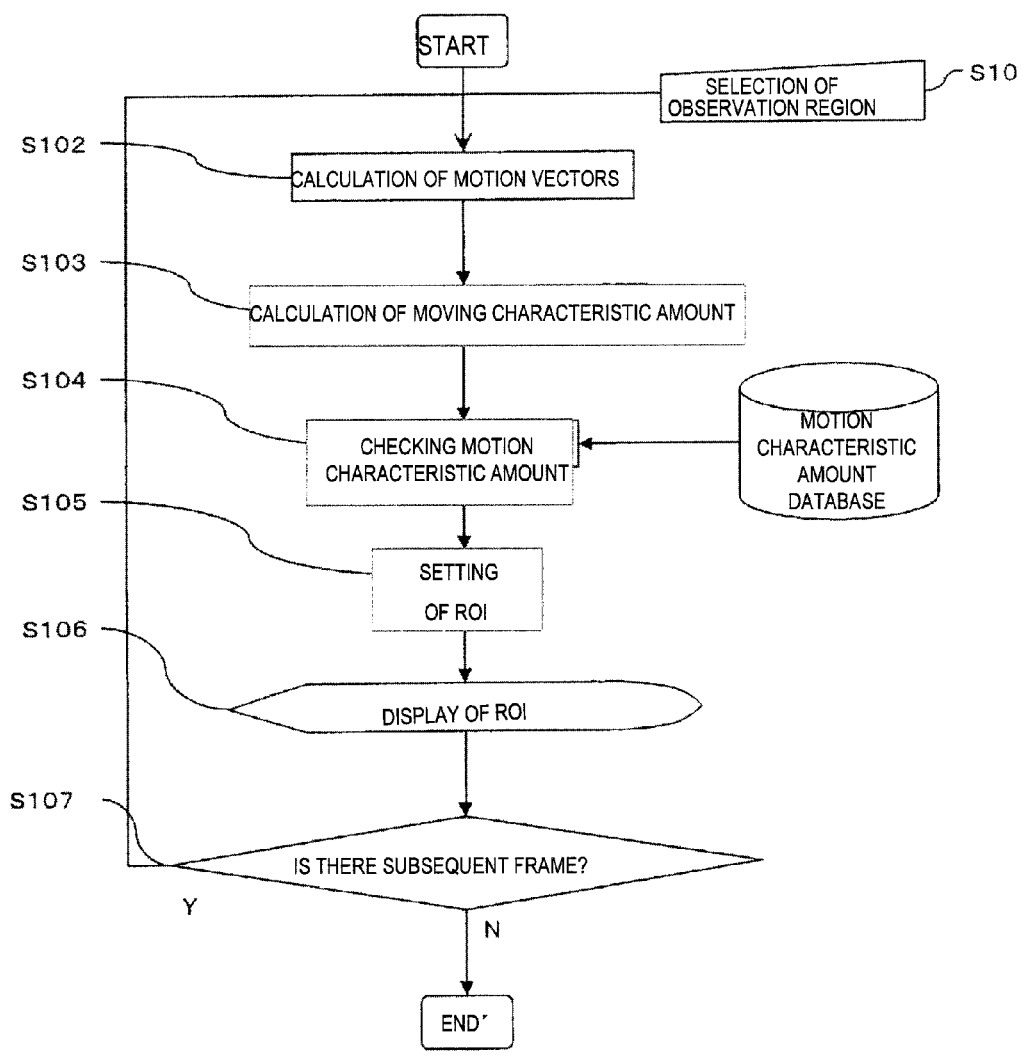
FIG. 3 is a flowchart of Example 1 of the ultrasonic diagnosis device.

Hereinafter, the operations of the ultrasonic diagnosis device will be described in detail. FIG. 3 is a flowchart of Example 1 of the ultrasonic diagnosis device. The present example is an example of automatically setting the ROI based on the motion vectors of the measurement points of the tomographic image of the object. First, the examiner selects an observation region for which it is desired to set the ROI by using the input portion 12 (S101). Herein, in selecting the observation region, candidates of the ROI can be displayed in advance in the list 204 as shown in FIG. 2, and the user can select the ROI by using the input portion 12. Moreover, it is possible to select one to plural ROIs from the list by using the trackball and a button, or to make a list of regions desired to be observed in advance so as to select the ROI using a foot switch or the like while switching the ROI in the order of the list. In addition to selecting the ROI by displaying the candidates of the ROI in the list 204, for example, it is also possible for the examiner to input an arbitrary observation region with texts or with a speech recognition function through a microphone.

In addition to the example in FIG. 2, the ROI can be prepared in various manners according to the purpose of observation or measurement for which the ROI should be set, such as the Doppler sample gate, color flow mapping, tissue Doppler, zoom observation, speckle tracking, and the like.

Subsequently, the motion vector calculation portion 8 calculates the motion vectors (S102). For example, as shown in the left side of FIG. 4, sample points 501 (measurement points) for calculating the motion vectors in the whole image are set, and motion vectors 502 of the sample points 501 are calculated. In the example at the left side of FIG. 4, the sample points 501 are positioned like a grid so as to cover the whole image. However, the arrangement method of the sample points 501 is not limited thereto. As the density of the sample points 501 increases, motion information of higher spatial resolution is obtained. However, this leads to an increase in calculation time. Therefore, it is also possible to position the sample points 501 by thinning out the sample points at appropriate intervals.

As a calculation method of calculating the motion vectors, a motion analysis using an amplitude pattern of the ultrasonic signals is used. A pattern matching method is used which uses the amplitude pattern around the sample points 501 to calculate a movement destination in the subsequent frame, and for example, a well-known method such as a block matching method or the like can be applied. The amplitude pattern used is an ultrasound RF signal output from the ultrasonic signal generation portion 5 and a two or three dimensional ultrasonic image pattern output from the ultrasonic image generation portion 6. In addition, the position and vectors of the sample points 501 may or may not be displayed on the measurement screen in practice.

In a case of a pulsatile tissue such as the heart or blood vessels, it is possible to set a time phase in which the motion vectors are calculated, in synchronization with the biosignals output from the biosignal detection portion 7. This time phase is controlled by the control portion 14. For example, when the target tissue is the heart, and the biosignal is ECG, by calculating the motion vectors from an R wave of ECG only for a certain period time, it is possible to effectively extract only the characteristic of the motion in systole. It is also possible to calculate the motion vectors only in one to plural certain time phases of ECG, without calculating the motion vectors continuously.

Thereafter, the motion characteristic amount is calculated (S103). When the process of S102 is performed, a time series data of the magnitude and direction of motion for each sample point, that is, a distribution pattern of the motion vectors is obtained. The distribution pattern of the motion vectors itself can also be taken as the characteristic amount. Furthermore, it is also possible to redefine the distribution pattern as a characteristic amount which is obtained by extracting the characteristic of the tissue motion, by further performing calculation. For example, it is possible to extract only a section of systole in synchronization with ECG. It is also possible to extract directional characteristics by calculating the hourly average of directional components of the motion vectors. If a tissue showing rapid motions, such as a valve, is focused, a maximum value of magnitude components of the motion vector is extracted, whereby the characteristic amount can be defined for each tissue.

Subsequently, the characteristic amount checking portion 9 checks the motion characteristic amount (S104). This is a process of detecting a position where the motion characteristic amount calculated in S103 coincides with the motion characteristic amount in the motion characteristic amount database 10. In the motion characteristic amount database 10, plural different observation regions in which the ROI is set and the motion characteristic amount thereof are held in association with each other. For example, in a case of the left ventricle, the distribution pattern of the motion vectors at sample points in the tomographic images of the respective observation regions can be set and stored in advance, so that the distribution pattern can be regarded as an average motion characteristic amount of the whole left ventricle (for example, the distribution pattern of the motion vectors appearing in the left ventricle). In addition, for example, since the cardiac valve moves most rapidly among other regions of the heart, it is also possible to store the characteristic amount in a logical form such as "position where magnitude of motion vector yields extreme value".

Figure 5:
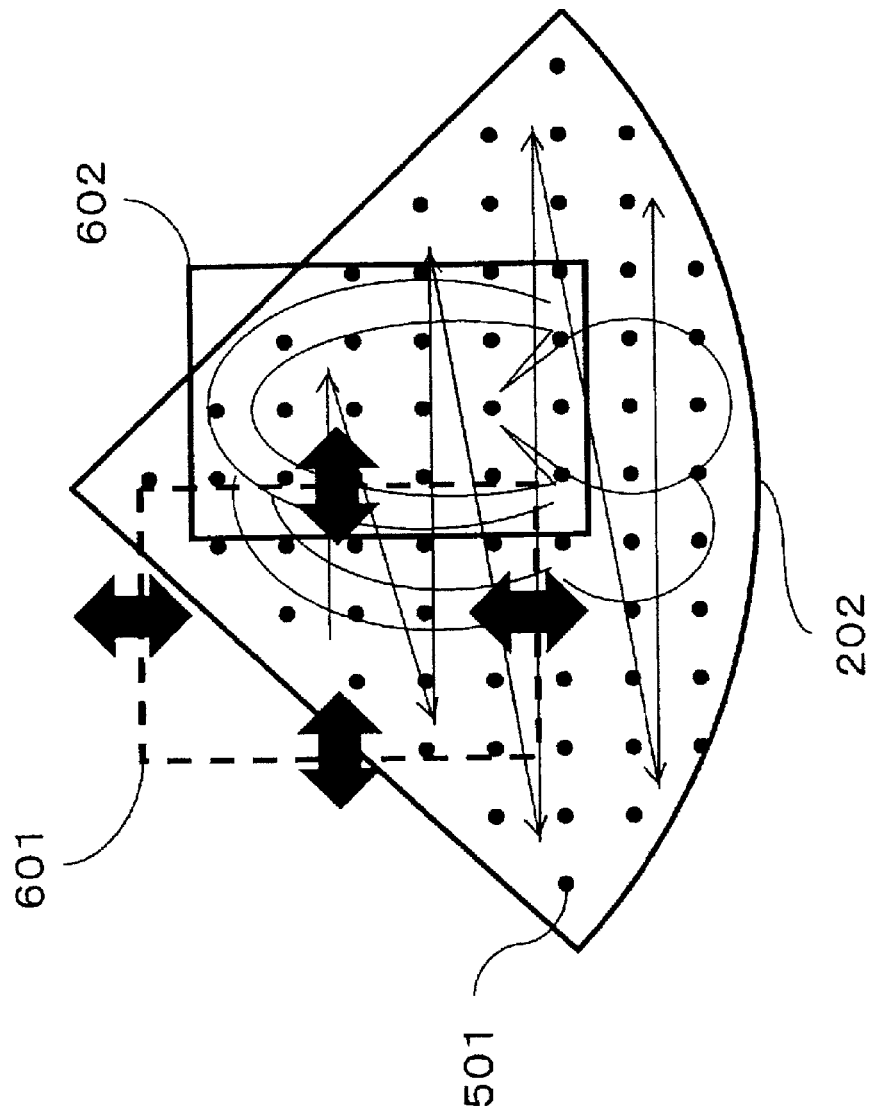
FIG. 5 is a view showing an example of checking a motion characteristic amount that is read from a database of the motion characteristic amount with a calculated motion characteristic amount of a tomographic image.

For example, when checking is performed using the average motion characteristic amount of the whole left ventricle (when the examiner specifies the whole left ventricle as the observation region), the motion characteristic amount corresponding to the whole left ventricle is read from the motion characteristic amount database 10 and checked with the calculated motion characteristic amount of the tomographic image. For example, while the position and size of a motion characteristic amount 601 read from the motion characteristic amount database 10 are changed as shown in FIG. 5, scanning is performed in the tomographic image following the arrows, and at the same time, a position 602 where the read characteristic amount matches best with the calculated motion characteristic amount is detected.

Figure 4:
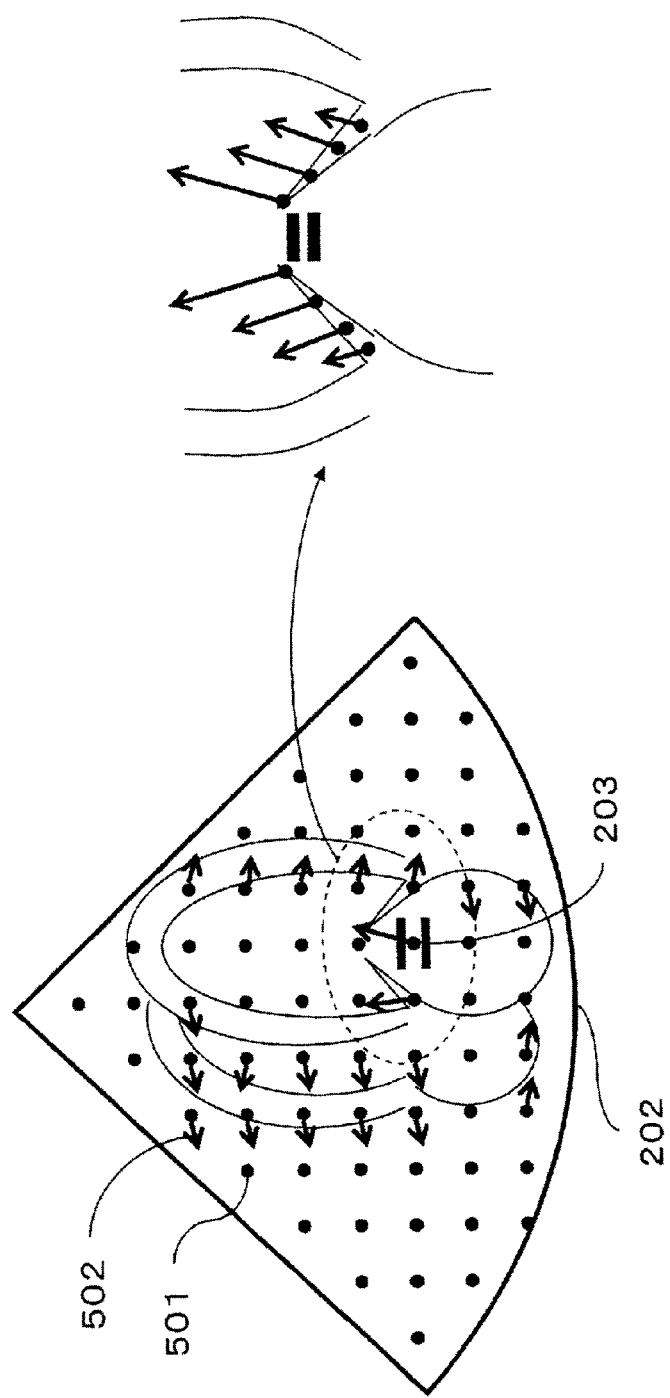
FIG. 4 is a view showing an example of setting a Doppler sample gate based on motion vectors in an apical 4-chamber view.
Figure 6:
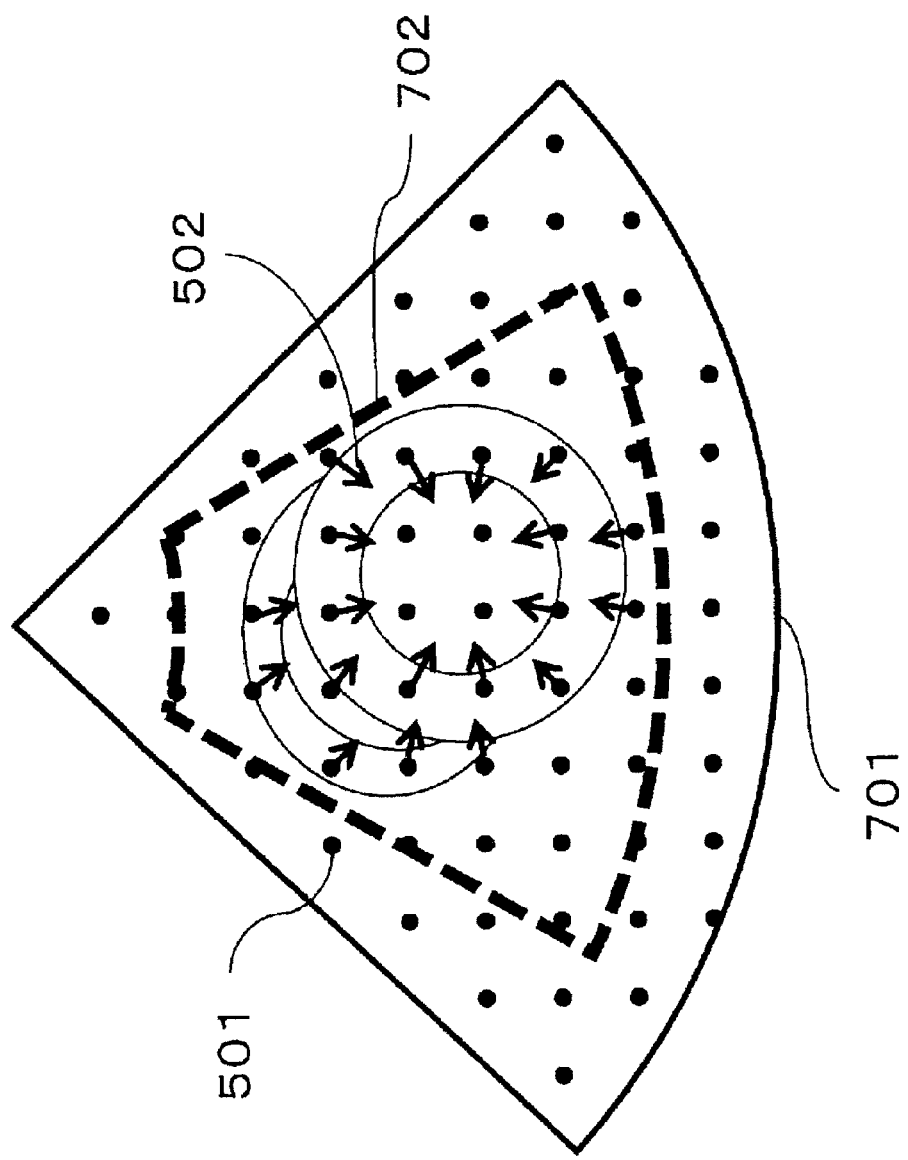
FIG. 6 is a view showing an example of setting a ROI in a short axis view of the heart based on the motion vectors.
Figure 7:
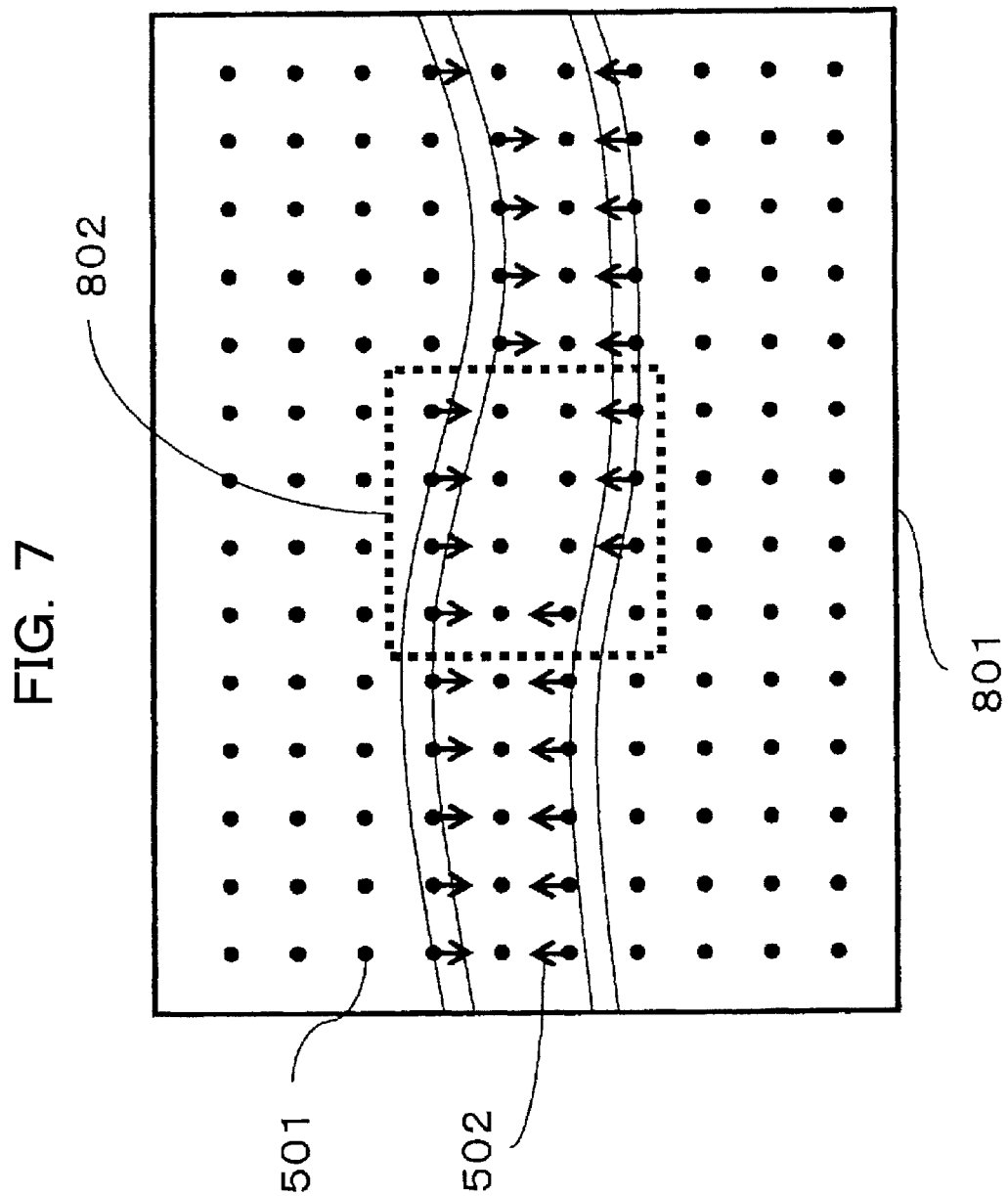
FIG. 7 is a view showing an example of setting the ROI in the carotid based on the motion vectors.

The shape of the ROI is set by the ROI setting portion 11 (S105). The size and position of the ROI is calculated by the processing described above. Therefore, according to the types (Doppler, two-dimensional, three-dimensional, and the like) of the ROI and measurement, the shape of the ROI is created and superimposed on the ultrasonic tomographic image. The shape of the ROI can be set according to the tissues and measurement items. The ROI can be shaped into the Doppler sample gate 203 as shown in FIG. 4, a quadrangle as shown in FIGS. 5 and 7, a fan-like ROI 702 as shown in FIG. 6, and a three-dimensional ROI in a three-dimension. When the position of the ROI is finely adjusted, it is also possible to manually adjust the position by using an input instrument such as the input portion 12.

The setting of the ROI will be described based on a couple of examples other than the example of the left ventricle. As in the case of the cardiac valve, when the "position where magnitude of motion vectors yields extreme value" is detected, a position where the magnitude of the motion vectors becomes maximal may be detected from the motion characteristic amount calculated in a target image. In the example in FIG. 4, a position where the magnitude of the vectors becomes maximal is detected, and the Doppler sample gate 203 is set. This example shows a case where the examiner selects the position in the list 204 so that the Doppler sample gate is positioned in MV, and in the drawing, the Doppler sample gate 203 is set.

The right side of FIG. 4 is an example of analyzing the left side of FIG. 4 in detail. The magnitude of velocity vectors of the valve at the right and left sides is small at the base and great at the tip. In addition, the directions of the vectors are opposite to each other toward the left and right directions. Consequently, if the sample gate is set in the center of vectors which show maximum velocity and faces opposite directions from each other, it is possible to set the ROI with a higher accuracy.

FIG. 6 is a view showing an example of setting the ROI in the short axis view of the heart based on the motion vectors. In an example (FIG. 6) 701 of the short axis view, if the characteristic amount is defined as a region having the magnitude of the motion vectors which is equal to or greater than a certain threshold, it is possible to set a fan-shaped ROI 702 surrounding the myocardium. In this manner, the ROI can be set with a simple procedure, and then operations such as observing the ROI closely by zooming-in the ROI, measuring the dynamic state of the myocardium from the motion vectors, and the like can be simply performed.

FIG. 7 is a view showing an example of setting the ROI in the carotid based on the motion vectors. In an example (FIG. 7) 801 of the carotid, by defining the characteristic amount as a region in which the directions of the motion vectors face each other, it is possible to set a ROI 802 surrounding the superior and inferior carotid walls. Thereafter, it is possible to simply perform operations such as observing the ROI closely by zooming-in the ROI, measuring the dynamic state of the walls from the motion vectors, setting the ROI for IMT (Intima-Media Thickness) measurement, and the like.

Subsequently, an ultrasonic image including the ROI is displayed on the measurement screen 201 by the output and display portion 13 (S106). As shown in FIG. 2, the Doppler sample gate 203 is displayed as the ROI while being superimposed on the apical 4-chamber view 202 of the heart in the measurement screen 201. The positional data of the ROI is output to a measurement processing portion for the subsequent processing, and the measurement is performed.

Subsequently, finally, whether there is a request for setting the ROI in the subsequent frame is confirmed (S107). If there is no such a request in the subsequent frame, the processing ends, and if there is a request, processing is repeated from S102. In this manner, it is possible to continuously detect the position of the ROI that moves continuously with time, even if the tissue position changes.

According to the example, the examiner just selects the observation region for which it is desired to set the ROI, whereby the position and size of the ROI are automatically set. Accordingly, the burden on the examiner is reduced. In addition, since the characteristics of motion are held as a database, it is possible to respond to the automatic setting of the ROI of the observation region which shows various motions of the object. Moreover, by synchronizing the characteristics of motion with the biosignals, it is possible to extract a sharper motion characteristic amount.

EXAMPLE 2

Figure 9:
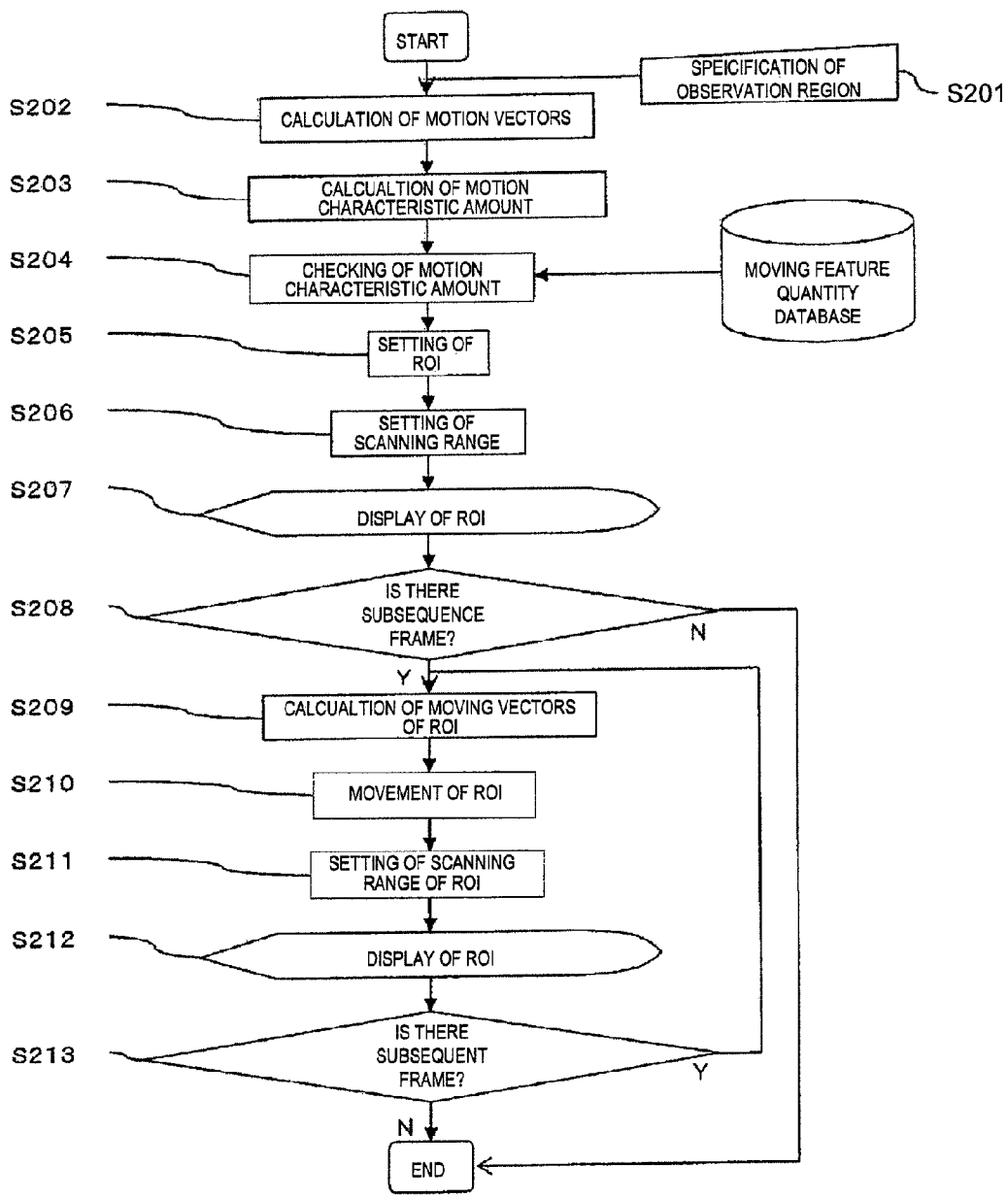
FIG. 9 is a flowchart of Example 2 of the ultrasonic diagnosis device.

Next, Example 2 of the ultrasonic diagnosis device to which the invention is applied will be described. The configuration of the ultrasonic diagnosis device of Example 2 is the same as Example 1. FIG. 9 is a flowchart of Example 2 of the ultrasonic diagnosis device. In Example 2, after the ROI is set in the same manner as in Example 1, a beam scanning range is narrowed down based on the set ROI, and the position of the ROI is caused to follow the tissue motion.

Figure 8:
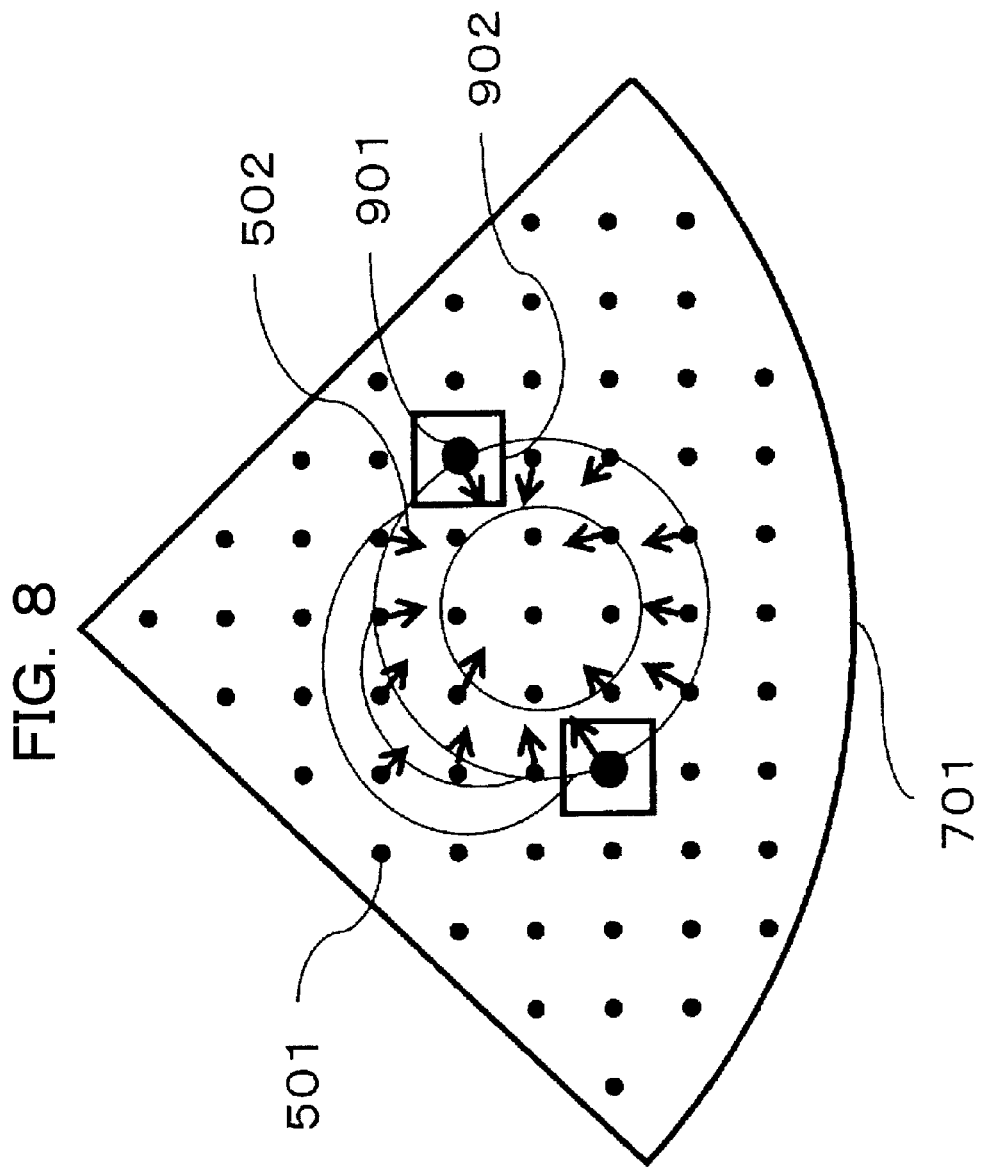
FIG. 8 is a view showing an example of setting the ROI at two locations in the short axis view of the heart based on the motion vectors.

Steps S201 to S205 are the same as steps S101 to S105 of Example 1, hence the description thereof is omitted. Herein, a case of setting a ROI 902 at two locations in the short axis view of the heart in FIG. 8 will be described for example. The myocardium of the heart repeatedly contracts and dilates while moving as if it twists. Accordingly, for example, if a characteristic amount defined as vectors that move obliquely toward a lower left side (or move obliquely toward an upper right side) while rotating is stored in advance, it is possible to set the ROI 902. In this manner, setting the ROI 902 at two locations is suitable for a case of measuring the change in distance between centers 901 of the ROI at two locations, or performing the Doppler measurement for 2 locations at the same time.

Figure 10:
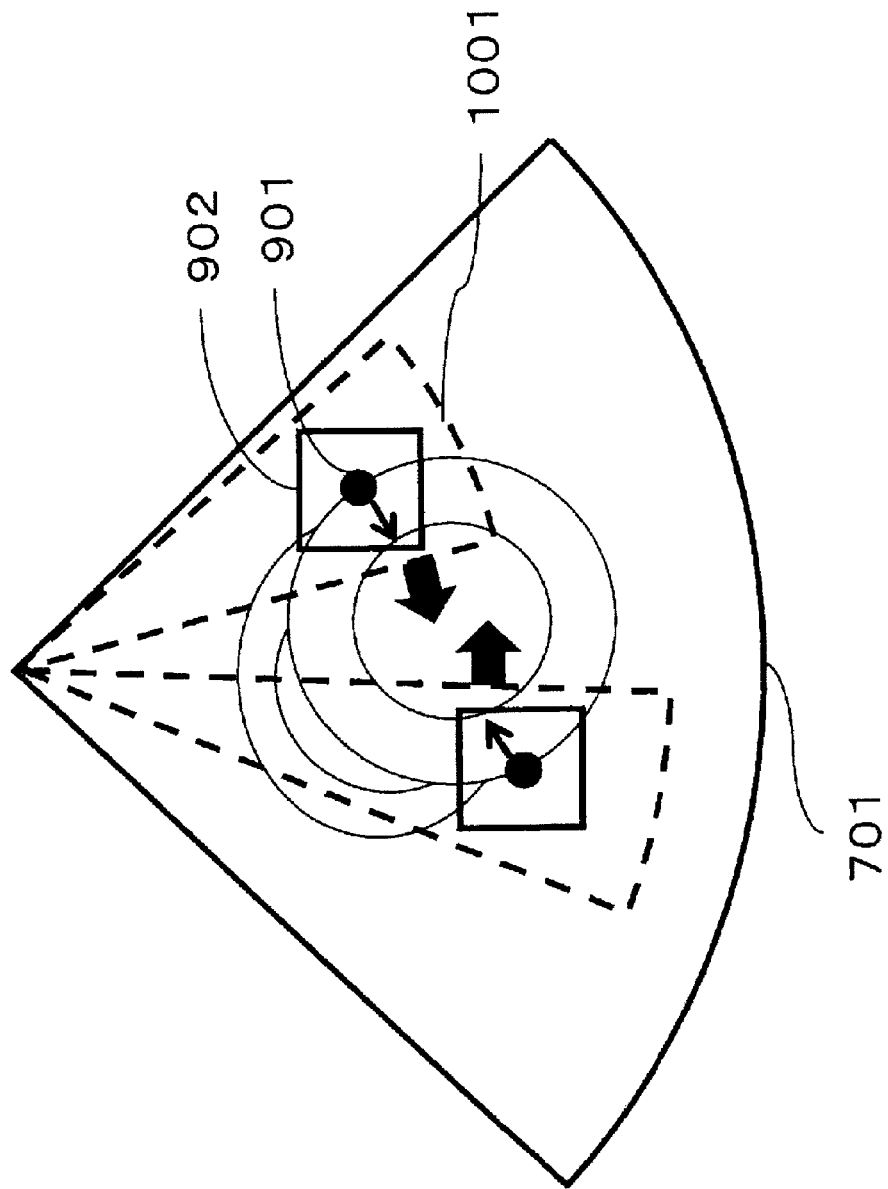
FIG. 10 is a view showing an example of changing scanning line density in an ultrasonic scanning range including the ROI and in an ultrasonic scanning range not including the ROI, and performing the following display of the ROI, as processing of Example 2 of the ultrasonic diagnosis device.

After the ROI is set in the ROI setting step S205, the beam scanning range is set (S206). The information on the set ROI is transmitted to the ultrasonic signal transmitting and receiving portion 4 from the ROI setting portion 11, and the scanning range is controlled by the ultrasonic signal transmitting and receiving portion 4. As shown in FIG. 10, the scanning line density is increased in the ultrasonic scanning range including the ROI 902, and the scanning line density is reduced in other ultrasonic scanning range not including the ROI 902, whereby the ranges are distinguished. In this manner, by increasing the number of scanning lines only in the ultrasonic scanning range including the ROI 902, it is possible to improve the image quality and measurement accuracy of the ROI 902.

Figure 11:
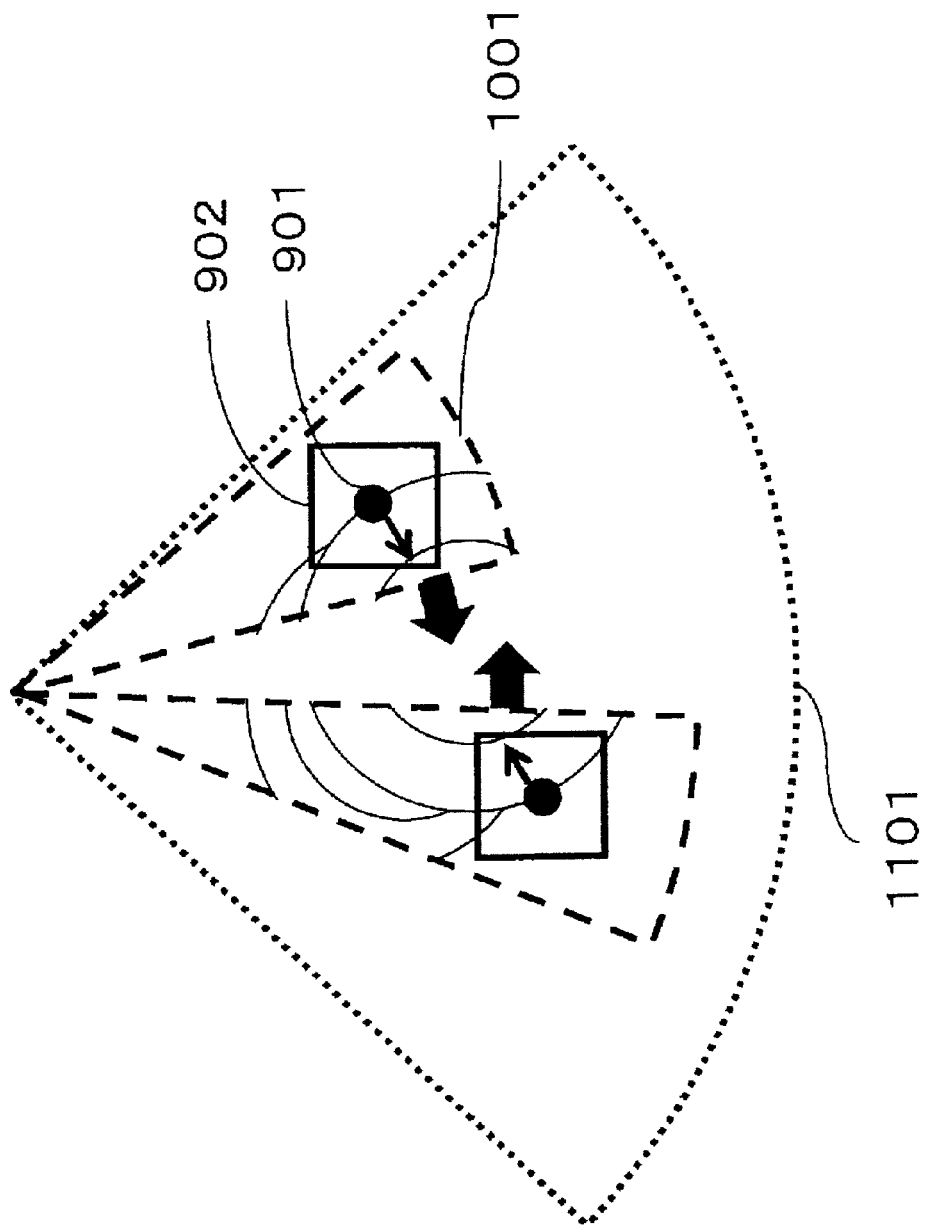
FIG. 11 is a view showing an example of performing ultrasonic scanning only on the ultrasonic scanning range including the ROI and performing the following display of the ROI, as the process of Example 2 of the ultrasonic diagnosis device.

As shown in FIG. 11, it is also possible to set the scanning lines in the range covering the ROI 902 so as not to scan regions out of this range. By performing the ultrasonic scanning only in the range of the ROI, the number of scanning lines per frame decreases. Therefore, it is possible to improve a frame rate and to improve the temporal resolution of the observation and the measurement.

Thereafter, the ROI is displayed by being superimposed on the ultrasonic tomographic image by the output and display portion 13 (S207). The shape or the like of the ROI is the same as in step S106 of Example 1. In the present example, the scanning line range is set variably, so the display is performed in response to the variations. In FIG. 10, since the scanning line density changes according to the range surrounding the ROI 902, a scanning line range 1001 is displayed so as to clearly show the change of the scanning line density. In FIG. 11, since only the scanning line range 1001 is scanned, it is shown that nothing is drawn in ranges outside the scanning line range 1001. It is also possible to display the initially captured tomographic image of the region other than the scanning line range 1001 of FIG. 11 and so as not to update the image.

Subsequently, whether there is a request for setting the ROI in the subsequent frame is confirmed (S208). If there is no such a request, the processing ends, and if there is a request, a process of causing the ROI to follow the tissue is performed as described below.

Thereafter, the motion vectors of the ROI are calculated by the motion vector calculation portion 8 (S209). As shown in FIG. 10, by using the amplitude pattern of the measurement points near the center 901 of the ROI, the movement destination in the subsequent frame is calculated. The details of the calculation of the motion vectors are the same as in step S102 of Example 1.

Next, the ROI setting portion 11 moves the ROI by the calculated motion vectors (S210). As shown in FIGS. 10 and 11, the ROI 902 is moved in a vector (thin arrow) direction from the center 901 of the ROI.

Then, the beam scanning range is set (S211). The information on the set ROI is transmitted to the ultrasonic signal transmitting and receiving portion 4 from the ROI setting portion 11, and the scanning range is controlled by the ultrasonic signal transmitting and receiving portion 4. The position of the ROI 902 moves. Therefore, in response to this movement, the scanning range should also be moved along the movement. FIGS. 10 and 11 show states where the position of the ROI moves in the thin arrow direction. According to the degree of this movement, the scanning range is moved by the thick arrow.

Subsequently, the ROI is displayed by the output and display portion 13, in a position determined by the ROI setting portion 11 (212). At the same time, the scanning line range 1001 is also displayed in a moved position.

Thereafter, whether there is a request for setting the ROI in the subsequent frame is confirmed (S213). If there is no such a request, the processing ends, and if there is a request, the processing is repeated from the step S209, whereby the process of causing the ROI to move and follow is performed.

Figure 12:
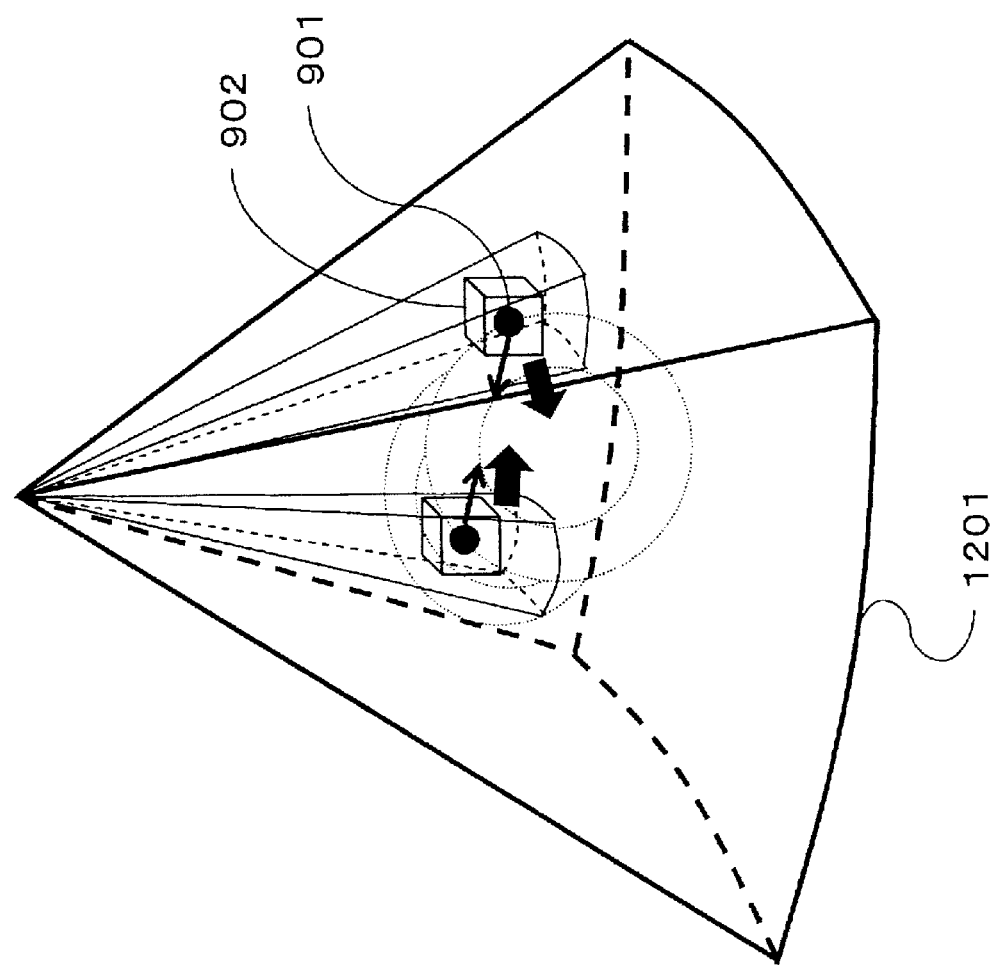
FIG. 12 is a view showing the display and following state of the ROI in a case where the process of Example 2 of the ultrasonic diagnosis device is applied to a three dimensional image.

Herein, regarding the case of the three-dimensional image, an example of imaging the heart by using a sector type two-dimensional array probe as shown in FIG. 12 will be described. This example can be applied to both the Examples 1 and 2 in a manner in which three-dimensional vectors are created by increasing the dimension in a depth direction. In this case, the motion vector calculation portion 8 determines motion vectors of plural measurement points of three-dimensional volume data that is generated based on plural sheets of tomographic images generated by the ultrasonic image generation portion 6. In addition, the motion characteristic amount checking portion 9 reads the characteristic amount of the observation region specified through the input portion 12 from the motion characteristic amount database 10, and checks the characteristic amount with the motion vectors of the generated three-dimensional volume data, which is calculated by the motion vector calculation portion 8.

In the case of FIG. 12, the ROI 902 is a cuboid, and the motion vectors are calculated using a three-dimensional amplitude pattern. As described above, the information on the set ROI is transmitted to the ultrasonic signal transmitting and receiving portion 4 from the ROI setting portion 11, and the scanning range two-dimensionally controls the oscillator array of the probe by the ultrasonic signal transmitting and receiving portion 4, whereby the direction of the beam is adjusted.

According to the present example, the position of the ROI and the scanning line range are moved in response to the tissue movement, and the ROI is caused to follow the tissue continuously. Accordingly, the examiner can reduce the time and effort involved in setting the ROI, and the measurement and observation of the temporal changes of a tissue become easy. Moreover, changing the scanning line density makes it possible to improve the image quality and the measurement accuracy by paying attention to the ROI.

EXAMPLE 3

Figure 13:
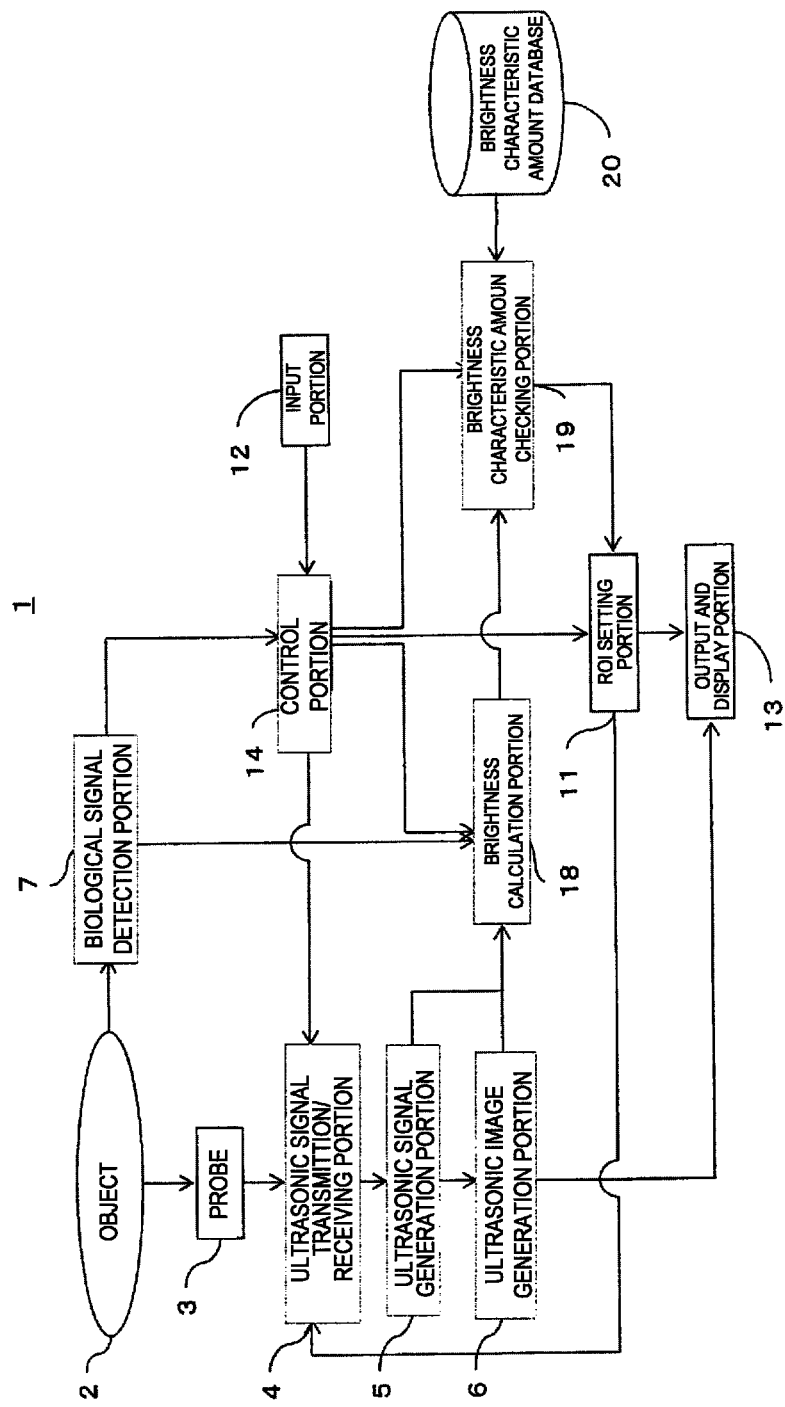
FIG. 13 is a block diagram showing a schematic configuration of Example 3 of the ultrasonic diagnosis device.

Next, Example 3 of the ultrasonic diagnosis device to which the invention is applied will be described. FIG. 13 is a block diagram showing a schematic configuration of the ultrasonic diagnosis device of Example 3. As shown in FIG. 13, in the ultrasonic diagnosis device 1 of the example, the motion vector calculation portion 8 of Example 1 is substituted with a brightness calculation portion 18, the motion characteristic amount checking portion 9 is substituted with a brightness characteristic amount checking portion 19, and the motion characteristic amount database 10 is substituted with a brightness characteristic amount database 20. Configurations other than these are the same as Example 1, so the descriptions thereof are omitted.

At timings and positions specified by the control portion 14, the brightness calculation portion 18 performs a statistical processing such as averaging, dispersion, and the like on a brightness distribution of plural measurement points of the tomographic image of the object 2 and other brightness distributions by using the ultrasonic signals output from the ultrasonic signal generation portion 5 and the amplitude pattern of the ultrasonic image output from the ultrasonic image generation portion 6, thereby calculating the characteristic amount from which noise has been removed.

The brightness characteristic amount checking portion checks the brightness distribution output from the brightness calculation portion 18 or the characteristic amount of the brightness distribution with the characteristic amount which is stored in the brightness characteristic amount database 20 of the observation region specified through the input portion 12, thereby detecting the desired position of the ROI. The brightness characteristic amount checking portion 19 also determines the shape of the ROI according to measurement items specified by the input portion 12.

In the brightness characteristic amount database 20, the characteristic amount of the brightness of measurement points in the respective tomographic images of plural different observation regions where the ROI is set is set and stored in advance. For example, a distribution pattern of the brightness of the plural measurement points in the tomographic images of the respective observation regions is stored. In addition, information on the shape of the ROI that should be set for each of the observation regions and the measurement items is stored.

Figure 14:
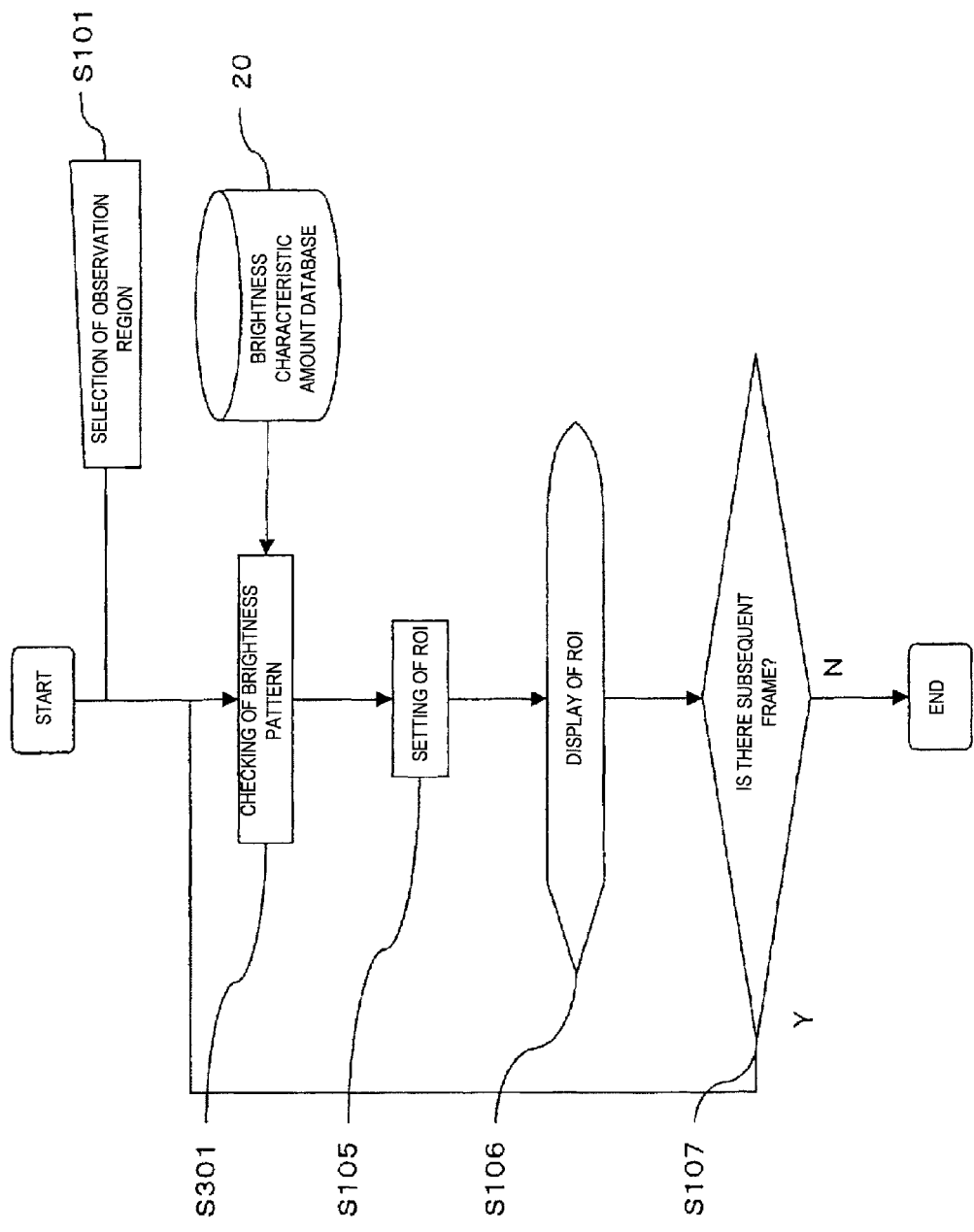
FIG. 14 is a view showing a processing flow of Example 3 of the ultrasonic diagnosis device.

FIG. 14 is a flowchart of Example 3 of the ultrasonic diagnosis device. Example 3 is an example of automatically setting the ROI by applying a pattern matching method that uses the characteristic of the brightness pattern of the observation region. In FIGS. 14, S102 to S104 of the processing flow (FIG. 3) of Example 1 are substituted with S301. Similarly, in the processing flow (FIG. 9) of Example 2, S202 to S204 can also be substituted with S301.

In S301, the brightness characteristic amount database 20 is referred to instead of the motion characteristic amount database 10. In the brightness characteristic amount database 20, the brightness distribution pattern of the measurement points in the tomographic images of plural different observation regions, for example, the brightness distribution patterns of all of the cardiac valves, myocardium, and cardiac chambers are stored.

In checking the brightness distribution pattern, as shown in FIG. 5, the brightness distribution pattern of a desired observation region, which is read from the brightness characteristic amount database 20, is used as data instead of the motion characteristic amount 601, scanning is performed in the tomographic image as shown by the arrow while the position and size are changed, and the position 602 that matches best is detected, whereby the ROI is set (S105).

According to the example, for example, even when it is difficult to set the ROI using the motion pattern since the heart shows abnormal motions due to a lesion, if the brightness pattern is used, it is possible to set the ROI in a still image, similarly to a case of using the motion pattern. Moreover, according to the example, it is possible to automatically set the ROI in various tissues that do not have motility, such as breast tissue, liver tissue, and the like. Therefore, the invention is suitable for setting the ROI in measuring and analyzing tumor sites of tissues.

In addition, it is possible to provide in parallel the motion vector calculation portion 8 with the brightness calculation portion 18, the motion characteristic amount checking portion 9 with the brightness characteristic amount checking portion 19, and the motion characteristic amount database 10 with the brightness characteristic amount database 20, in the ultrasonic diagnosis device 1. In this case, it is also possible to select a suitable one between the motion vectors and the brightness depending on the observation region. Moreover, if both the automatic ROI setting based on the motion vectors and the automatic ROI setting based on the brightness can be applied to an observation region, both of them are processed in parallel and displayed so as to let the examiner select one of them. In this manner, it is possible to improve the setting accuracy of the ROI.

EXAMPLE 4

Figure 15:
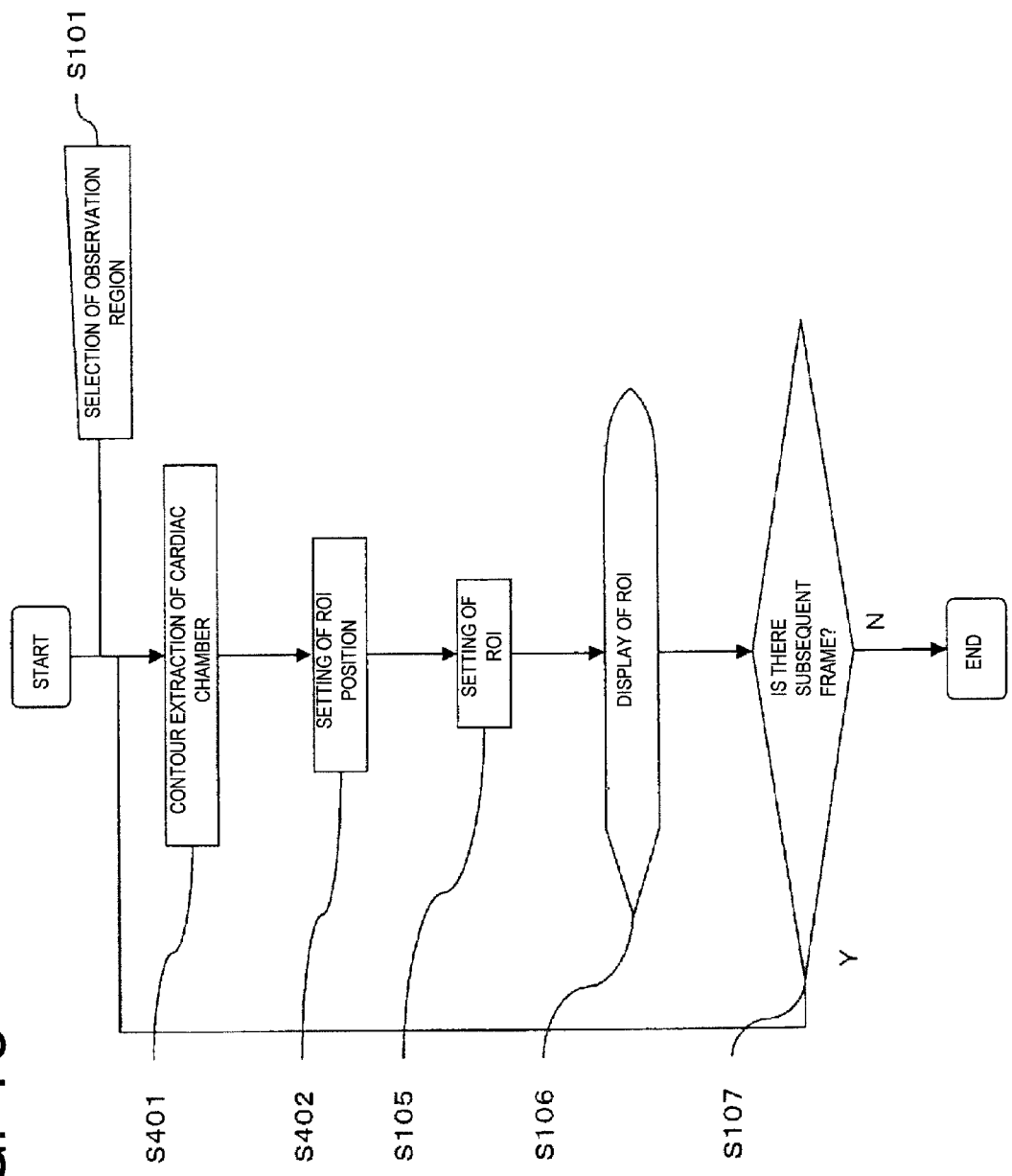
FIG. 15 is a view showing a processing flow of Example 4 of the ultrasonic diagnosis device.

FIG. 15 is a view showing a processing flow of Example 4 of the ultrasonic diagnosis device. Example 4 is an example of setting the ROI based on the contour of the cardiac chamber extracted using contour extraction calculation. As shown in FIG. 15, in the example, S102 to S104 of the processing flow (FIG. 3) of Example 1 are substituted with S401 to S402. Similarly, in the processing flow (FIG. 9) of Example 2, S202 to S204 can also be substituted with S401 to S402. Similarly, in the processing flow (FIG. 14) of Example 3, S301 can also be substituted with S401 to S402.

Figure 16:
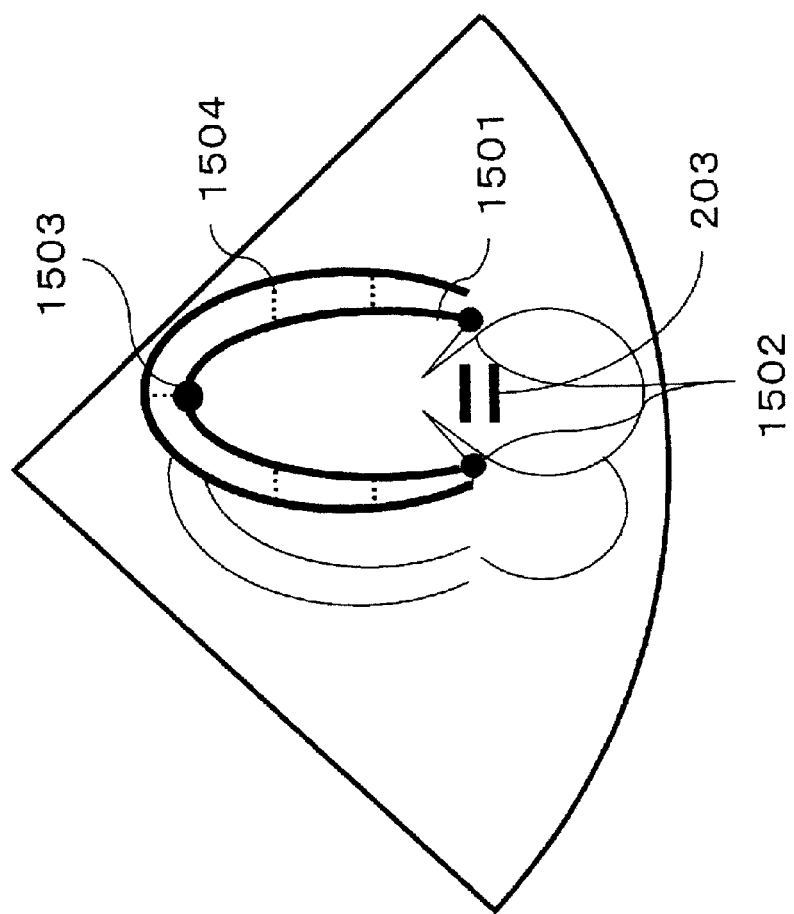
FIG. 16 is a view illustrating a process of setting the ROI from cardiac contour information, as Example 4 of the ultrasonic diagnosis device.

First, the contour of the cardiac chamber is extracted (S401). Existing methods can be used as the extraction method. For example, a method of using edge detection or a contour model is used. FIG. 16 is a view illustrating a process of setting the ROI from the cardiac contour information of Example 4. Thick solid line in FIG. 16 is created by extracting endocardium and epicardium contours 1501 of the left ventricle.

When the contour is extracted, various types of positional information that can be determined from the contour information are obtained on the contour. The cardiac contour is the contour of the cardiac chamber region that is surrounded by the inner wall of the cardiac chamber and the valve annulus surface. Consequently, both end points of the contour correspond to a valve annulus portions 1502, and the vertex thereof corresponds to a cardiac apex 1503. In addition, boundary lines 1504 of segmentation according to myocardial local segmentation which is recommended by the ASE (American Society of Echocardiography) are obtained. The positional relationship of the region is determined from the contour. Therefore, it is possible to set the desired position of the ROI, such as the whole left ventricle, a local myocardial position, the valve annulus portion, and the like (S402).

In addition to the case of setting the ROI on the contour as described above, for example, in a case of measuring the cardiac blood flow, if the center of the left and right valve annulus portions 1502 is set in advance as the characteristic amount, it is possible to automatically set the Doppler sample gate 203.

According to the present example, by using a method of obtaining the cardiac structure such as a contour, it is possible to ascertain the positional relationship of a region. Consequently, it is possible to set the various types of ROI similarly to other examples.

In each of the examples described above, the ultrasonic diagnosis device as an embodiment of the medical image diagnosis device, and the region-of-interest setting method in the ultrasonic diagnosis device as an embodiment of the region-of-interest setting method are described. However, the invention is not limited thereto. For example, the invention can be applied to a medical image processing device such as a PC that is used for performing various measurements, analyses, and the like by automatically setting the ROI online with respect to the tomographic image of an object which is generated in advance by a medical image diagnosis device or the like. In addition, the invention can also be applied to a region-of-interest setting program that is combined with the medical image processing device such as a PC and the like.

That is, the medical image processing device to which the invention is applied includes image input means for inputting a tissue image (a tomographic image of a tissue of a cross-sectional region) of an object generated in advance, calculation means for calculating at least one of brightness and motion vectors of plural measurement points of the input image (tomographic image), input means for specifying an observation region of the image (tomographic image), checking means for reading the characteristic amount of the observation region that is specified through the input means from a database in which the characteristic amount of at least one of the brightness and the motion vectors of the measurement points in the respective images (tomographic images) of plural different observation regions is set and stored, and checking the characteristic amount with results of the calculation performed on the image (tomographic image) by the calculation means, and ROI setting means for setting the region of interest in the image (tomographic image) based on checked results of the checking means.

For example, the examiner saves the image (tomographic image) of the object that is generated by the medical image diagnosis device such as the ultrasonic diagnosis device, in an information recording medium such as USB, USM, and the like, and inputs the image in the medical image processing device such as a PC through the image input means. Alternatively, it is also possible for the examiner to input the tomographic image of the object through a network without using the information recording medium.

Thereafter, the calculation means of the medical image processing device executes a step of calculating at least one of the brightness and the motion vectors of the plural measurement points of the input image (tomographic image), as a region-of-interest setting program. In addition, in a step of specifying the observation region of the image (tomographic image), the examiner specifies a region for which it is desired to set the region of interest, that is, the observation region, through the input means such as a mouse, a keyboard, a trackball, and the like of the medical image processing device. The checking means reads the characteristic amount of the observation region that is specified in the step of specifying the observation region from the database, and executes a step of checking the characteristic amount with at least one of the brightness and motion vectors of the plural measurement points of the image (tomographic image). The ROI setting means executes a step of automatically setting the region of interest in the image (tomographic image) based on the checked result. These steps executed by the medical image processing device are executed in substantially the same manner as the processing described in Examples 1, 3, and 4. Moreover, the function of giving a distinction regarding the scanning line density between the ultrasonic scanning range including the ROI and the ultrasonic scanning range not including the ROI, which is described in Example 2, a function of the following display of the ROI, and the like can also be combined with the medical image processing device.

In this manner, when the examiner specifies offline a region (observation region) for which it is desired to set the region of interest through the input means of the medical image processing device, the characteristic amount of the specified observation region is checked with the tomographic image read from the database, and the region of interest is automatically set in the images (tomographic images) based on the checking result. Accordingly, if the characteristic amount of various observation regions of the object, that is, a characteristic that appears uniquely in at least one of the brightness and the motion vectors of the measurement points of the image (tomographic image) of the respective observation regions, is calculated in advance and stored in the database, it is possible to automatically set the region of interest in the various observation regions of the object.

Moreover, although the tomographic image is taken as a target of setting the region of interest in the above embodiments, the target for setting the region of interest may be an M mode image, a tissue Doppler image, and the like.

REFERENCE SIGNS LIST 1 ultrasonic diagnosis device, 3 probe, 4 ultrasonic signal transmitting and receiving portion, 5 ultrasonic signal generation portion, 6 ultrasonic image generation portion, 7 biosignal detection portion, 8 motion vector calculation portion, 9 motion characteristic amount checking portion, 10 motion characteristic amount database, 11 ROI setting portion, 12 input portion, 13 output and display portion, 18 brightness calculation portion, 19 brightness characteristic amount checking portion, 20 brightness characteristic amount database, 501 sample point, 502 motion vector

The invention claimed is:

1. A medical image diagnosis device comprising:
an image generator configured to obtain image data of a tissue of an object and generate an image of the tissue of the object based on the image data;
a calculator configured to calculate motion vectors of a plurality of measurement points of the generated image to obtain a first motion characteristic amount;
an input instrument configured to specify an observation region of the image;
a database in which a characteristic amount of the motion vectors of the plurality of measurement points in respective images of a plurality of different observation regions is set and stored in advance;
a checker configured to read a second motion characteristic amount of the observation region specified by the input instrument from the database and detect a position where the first motion characteristic amount coincides with the second motion characteristics amount; and
an ROI (region of interest) setting unit configured to set a region of interest in the generated image based on the position where the first motion characteristic amount coincides with the second motion characteristic amount.

2. A medical image diagnosis device according to claim 1, wherein the image generator is a tomographic image generator configured to obtain image data of a tissue of an object and generate a tomographic image of the tissue of the object based on the image data.

3. The medical image diagnosis device according to claim 2,
wherein the calculator calculating the motion vectors of a plurality of measurement points of three-dimensional volume data that is generated based on a plurality of tomographic images generated by the tomographic image generator, and
wherein the checker reads the characteristic amount of the observation region that is specified through the input device, from a database in which the characteristic amount of the motion vectors of the plurality of measurement points in the respective three-dimensional volume data of a plurality of different observation regions is set and stored, and checks the characteristic amount with the calculation results of the generated three-dimensional volume data calculated by the calculator.

4. The medical image diagnosis device according to claim 1,
wherein the characteristic amount is set based on at least one of a distribution pattern of the motion vectors, and the magnitude and direction of the motion vectors of the plurality of measurement points in the respective images of the plurality of different observation regions.

5. The medical image diagnosis device according to claim 1,
wherein the characteristic amount includes the one which is set based on contour information of cardiac chamber region that is surrounded by an intra-cardiac chamber wall surface and a valve annulus surface, which is extracted from the distribution pattern of the plurality of measurement points in the cardiac image of the object.

6. The medical image diagnosis device according to claim 1,
wherein the region of interest set automatically by the ROI setting unit is displayed together with the generated image on display means, and is caused to follow the motion vectors of the plurality of measurement points of the image.

7. The medical image diagnosis device according to claim 1,
wherein the tomographic image generator includes an ultrasonic probe that transmits and receives ultrasonic waves to and from the object, an ultrasonic signal transmitting and receiving portion that transmits signals to the ultrasonic probe and receives reflected echo signals measured by the ultrasonic probe, an ultrasonic signal generating portion that generates an RF signal frame data of a cross-sectional region of the object based on the reflected echo signals, and an ultrasonic image generating portion that generates an ultrasonic tomographic image by performing a signal processing on the RF signal frame data, and
wherein the ultrasonic signal transmitting and receiving portion makes a difference in a setting for ultrasonic wave transmitting and receiving between an ultrasonic scanning region including the region of interest set by the ROI setting unit and an ultrasonic scanning region not including the region of interest.

8. The medical image diagnosis device according to claim 1 further comprising:

biosignal detecting means for detecting biosignals of the object, wherein in the calculator, a time phase is set which is for calculating the motion vectors of the plurality of measurement points of the tomographic image in synchronization with the detected biosignals.

9. A region-of-interest setting method comprising:

a step of obtaining image data of a tissue of an object and generating an image of the tissue of the object based on the image data;

a step of calculating motion vectors of a plurality of measurement points of the generated image to obtain a first motion characteristic amount;

a step specifying an observation region of the image;

a step a reading a second motion characteristic amount of the observation region specified in the step of specifying the observation region from a database in which the characteristic amount of the motion vectors of the plurality of measurement points in respective images of a plurality of different observation regions is set and stored, and detecting a position where the first motion characteristic amount coincides with the second motion characteristic amount; and a step of setting a region of interest in the generated image based on the position where the first motion characteristic amount coincides with the second motion characteristic amount.

10. The region-of-interest setting method according to claim 9, wherein the characteristic amount is based on at least one of a distribution pattern of the motion vectors, and the magnitude and direction of the motion vectors of the plurality of measurement points in the respective images of the plurality of different observation regions.

11. A medical image processing device comprising:

an image input instrument configured to input an image of a tissue of an object, which is generated in advance;

a calculator configured to calculate motion vectors of a plurality of measurement points of the input image to obtain a first motion characteristic amount;

an input instrument configured to specify an observation region of the image;

a checker configured to read a second motion characteristic amount of the observation region specified by the input instrument from a database in which the characteristic amount of the motion vectors of the plurality of measurement points in respective images of a plurality of different observation regions is set and stored, and detecting a position where the first motion characteristic amount coincides with the second motion characteristic amount; and an ROI (region of interest) setting unit configured to set a region of interest in the image based on the position where the first motion characteristic amount coincides with the second motion characteristic amount.

12. The medical image processing device according to claim 11, wherein the characteristic amount is based on at least one of a distribution pattern of the motion vectors, and the magnitude and direction of the motion vectors of the plurality of measurement points in the respective images of the plurality of different observation regions.

* * * * *